US005648338A

United States Patent [19]
Kakkar et al.

[11] Patent Number: 5,648,338
[45] Date of Patent: Jul. 15, 1997

[54] INHIBITORS AND SUBSTRATES OF THROMBIN

[75] Inventors: Vijay Vir Kakkar, Bickley; John Joseph Deadman, Sutton; Goran Karl Claeson, London; Leifeng Cheng, Oxford, all of Great Britain; Naoyashi Chino, Osaka, Japan; Said Mohamed Anwar Elgendy, London; Michael Finbarr Scully, Crays Hill, both of Great Britain

[73] Assignee: Thrombosis Research Institute, London, Great Britain

[21] Appl. No.: 317,837

[22] Filed: Oct. 4, 1994

Related U.S. Application Data

[63] Continuation of Ser. No. 158,046, Nov. 24, 1993, abandoned, which is a continuation of Ser. No. 866,178, filed as PCT/GB91/01946, Nov. 6, 1991, abandoned.

[30] Foreign Application Priority Data

Nov. 6, 1990 [GB] United Kingdom ............... 9024129.0

[51] Int. Cl.$^6$ .................... A61K 38/00; C07K 5/00; C07K 7/00
[52] U.S. Cl. .................. 514/18; 530/300; 530/331
[58] Field of Search ............... 514/18; 530/331, 530/300

[56] References Cited

U.S. PATENT DOCUMENTS 5,288,707 2/1994 Metternich ................... 514/19

Primary Examiner—Avis M. Davenport
Attorney, Agent, or Firm—Townsend and Townsend and Crew LLP

[57] ABSTRACT

Peptides which act as inhibitors or substrates of thrombin are derived from the formula: D-Phe-Pro-Arg or its analogues, wherein Phe is substituted by (a), wherein $Ar_1$ or $Ar_2$ are the same or different and are selected from the group consisting of phenyl, thienyl, pyridyl, naphthyl, thionaphtyl, indolyl and saturated groups corresponding to these, optionally substituted by up to three groups selected from $C_1$–$C_3$ alkyl and $C_1$–$C_3$ alkoxy, $L_1$ and $L_2$ are the same of different and are selected from the group consisting of $CH_2$, $C_2$—$C_2$, O-$CH_2$, S-$CH_2$, Ar-L taken together optionally means H, diphenyl-methyl, fluorenyl or saturated groups corresponding to these, but one of the Ar-L cannot be H when the other [$CH_2]_n$-Q, (c) where Q=H, amino, amidino, imidazole, guanidino or isothioureido and n=1–5, preferably 3–5, or $C_3$–$C_9$ alkyl and $C_5$–$C_{10}$ aryl or alkylaryl optionally substituted by up to three groups selected from hydroxy and $C_1$–$C_4$ alkoxy; Z=CN, $COR_1$, (d) or (e), where $R_1$=H, OH, $CH_2Cl$, $CH_2$—$C_2$—CO—pip, $CF_2$—$CF_2$—CO—pip, (f), (g), $CH_2$—$C_2$—CO—Pro—NHEt, $CF_2$—$CF_2$—CO—Pro—NHEt or a chromophoric group e.g. pHA, MCA, $R_2$ and $R_3$ are the same or different and are selected from the group consisting of OH, $OR_6$ and $NR_6R_7$, or $R_2$ and $R_3$ taken together represent the residue of a diol; where $R_6$ and $R_7$, which are the same or different, are $C_1$–$C_{10}$ alkyl, phenyl or $C_6$–$C_{10}$ arylalkyl, $R_4$ and $R_5$ are the same or different and are selected from $R_2$, $R_3$, Gly-pip, Ala-pip or Gly-Pro-NHEt.

29 Claims, No Drawings

INHIBITORS AND SUBSTRATES OF THROMBIN

This is a continuation of application Ser. No. 08/158,046 filed Nov. 24, 1993, and now abandoned, which is a continuation of application Ser. No. 07/866,178, filed as PCT/GB91/01946, Nov. 6, 1991, and now abandoned, and earlier international applications of record.

This invention relates to thrombin inhibitors and substrates.

Thrombin, the last enzyme in the coagulation system, cleaves soluble fibrinogen to fibrin, which is then crosslinked and forms an insoluble gel forming the matrix for a thrombus. When a vessel is damaged, the above process is necessary to stop bleeding. Under normal circumstances there is no measurable amount of thrombin present in plasma. Increase of the thrombin concentration can result in formation of clots, which can lead to thromboembolic disease, one of the most common serious medical problems of our time.

Thrombin contributes to haemostatic control by means of several biological reactions. In addition to its primary function, the conversion of fibrinogen to fibrin, thrombin activates Factor XIII, which is responsible for the crosslinking of fibrin. Thrombin also acts by means of a positive feedback mechanism involving the activation of Factors V and VIII, which both are necessary for its own formulation from prothrombin. Thrombin has another essential role: its binding to platelets initiates platelet release and aggregation which is responsible for primary haemostasis.

Fibrinolysis is the process which causes an enzymatic dissolution of fibrinogen and fibrin clots. Plasma contains a protein, plasminogen, which under the influence of various activators is converted to plasma, a proteolytic enzyme, the activity of which resembles that of fibrin. Plasmin breaks down fibrin to fibrin degradation products.

Under normal conditions, the fibrinolysis system is in balance with the coagulation system. Small thrombi formed in the blood stream can be dissolved enzymatically and the circulation through the vessels can be restored by the activation of the fibrinolytic system in the body. If the fibrinolytic activity is too high, it may cause or prolong bleeding and if it is too low compared to the activity of the coagulation system, there is a risk of thrombosis.

The reactions of thrombin are further controlled by natural inhibitors in plasma. The most important of these are antithrombin III and heparin. These two compounds have been isolated and are therapeutically and prophylactically used in conditions where there is an imbalance in the haemostatic mechanisms with risk for prothrombin activation.

Mainly two types of therapeutic agents are used for the prevention of thrombosis. The heparins act by accelerating the inhibition of thrombin by antithrombin III. Coumarin derivatives, the oral anticoagulants, e.g. Warfarin, prevent the generation of thrombin by blocking the post-translational vitamin K-dependent α-carboxylation in the synthesis of prothrombin. Neither Heparin nor Warfarin are ideal. Heparin must be given parenterally and as it functions as a cofactor to antithrombin III it has no effect without this inhibitor. The effect of Warfarin develops very slowly and individual doses must be adjusted by frequent tests. None of these anticoagulants is specific for thrombin, they also inhibit other serine proteases and both of them may cause bleeding if the doses are not correctly balanced.

Thus, direct acting, specific thrombin inhibitors, having oral activity would be useful alternatives to the above anticoagulants. Much research in this area has resulted in the synthesis of different kinds of inhibitors of thrombin.

By imitating amino acid sequences of fibrinogen, the important natural substrate of thrombin, several good short peptide substrates for thrombin have been synthesized. The very first developed sequence with affinity for the active site of thrombin was Phe-Val-Arg [1] which mimics the fibrinogensequence preceding the bond split by thrombin. This sequence has later been improved to give D-Phe-Pro-Arg and D-Phe-Pip-Arg which have been used in chromogenic substrates, e.g. D-Phe-Pro-Arg-pNA and D-Phe-Pip-Arg-pNA[1] and in inhibitors of thrombin, e.g. the peptide aldehyde D-Phe-Pro-Arg-H [2], the irreversible inhibitor D-Phe-Pro-Arg-CH$_2$Cl [3], inhibitors with a ketomethylene bond e.g. D-Phe-Pro-Arg-K-Gly-piperidide [4] and in the recently synthesized peptide boronic acid inhibitors e.g. Z-D-Phe-Pro-boroArg [5] and the nitrile: Boc-D-Phe-Pro-ArgCN [6].

Thus, D-Phe-Pro-Arg has been considered the best sequence for about 15 years, and it has been shown to have very good affinity for the active site of thrombin, in substrates (Km around $10^{-6}$M) as well as in inhibitors (Ki $10^{-7}$M to $10^{-9}$M).

We have now found that by exchanging Phe, in the D-Phe-Pro-Arg sequence, for some unnatural, aromatic amino acids, with a specified structure, and by using these new sequences to construct novel substrates and inhibitors we obtained significantly improved substrate and inhibitor properties. The new substrates show better kinetic constants (Km and kcat) and the inhibitors better inhibition constant (Ki).

Reduction of blood pressure is a side effect observed in many of the previous thrombin inhibitors containing Arg or Arg analogues like Gpa and Apa [7]. This side effect which in some compounds can be disturbingly serious is believed to depend on the positively charged guanidino or amidino group of the side chain of Arg or its analogues. Surprisingly, this side effect of inhibitors in the present application is markedly reduced even when the inhibitors have an Arg or Arg analogue.

We have also surprisingly found that by changing the side chain to a non-basic alkyl or alkylaryl group of a certain size, the affinity for thrombin is still very good although the affinity for other serine proteases is greatly reduced, i.e. these inhibitors/substrates are more specific for thrombin than corresponding compounds containing Arg. With this non-basic side chain the blood pressure lowering side effect is greatly reduced.

The present invention provides thrombin inhibitors and substrates derived from D-Phe-Pro-Arg or its analogues wherein Phe is substituted by

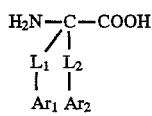

and Arg may be substituted by

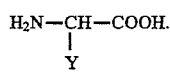

Suitably, the inhibitors/substrates are of formula I, in which

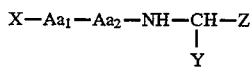    I

X=H, CH₃ or an N-protecting group, e.g. Ac, Bz, Cbz, Boc;
Y=[CH$_2$]$_n$–Q,

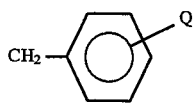

where Q=H, amino, amidino, imidazole, guanidino or isothioureido and n=1–5, preferably 3–5, or $C_3$–$C_9$ alkyl and $C_5$–$C_{10}$ aryl or alkylaryl optionally substituted by up to three groups selected from hydroxy and $C_1$–$C_4$ alkoxy:
Z=CN, COR$_1$,

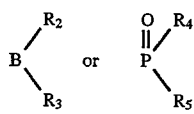

where
R$_1$=H, OH, CH$_2$Cl, CH$_2$I3 C$_2$—CO—pip, CF$_2$—C$_2$—CO—pip,

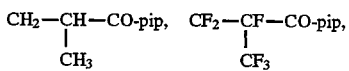

CH$_2$—CH$_2$—CO—Pro—NHEt, CF$_2$—CF$_2$—CO—Pro—NHEt or a chromophoric group e.g. pNA, MCA, R$_2$ and R$_3$ may be the same or different and are selected from the group consisting of OH, OR$_6$ and NR$_6$R$_7$, which may be the same or different, are $C_1$–$C_{10}$ alkyl, phenyl or $C_6$–$C_{10}$ arylalkyl, R$_4$ and R$_5$ may be the same or different and are selected from R$_2$, R$_3$, Gly-pip, Ala-pip or Gly-Pro-NHEt;

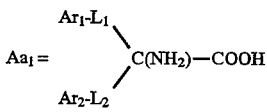

where
Ar$_1$ and Ar$_2$ may be the same or different and are selected from the group consisting of phenyl, thienyl, pyridyl, naphthyl, thionaphthyl, indolyl and saturated groups corresponding to these, optionally substituted by up to three groups selected from $C_1$–$C_3$ alkyl and $C_1$–$C_3$ alkoxy,
Lhd 1and L$_2$ may be the same or different and are selected from the group consisting of CH$_2$, CH$_2$—CH$_2$, O—CH$_2$, S—CH$_2$,
Ar-L taken together may mean H, diphenyl-methyl, fluorenyl or saturated groups corresponding to these, but on of the Ar-L cannot be H when the other Ar-L means H or benzyl;

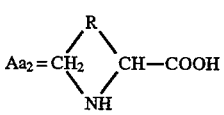

or its $C_1$–$C_3$ alkyl substituted derivatives, where R$_8$=CH$_2$, CH$_2$—C$_2$, S—CH$_2$, S—C(CH$_3$)$_2$ or CH$_2$—CH$_2$—CH$_2$.

Preferably the Phe substitute is Dpa, Nal or Dba and preferable Arg substitute includes Irg, Gpa, Apa and non-basic amino acids such as Pgl, Mbg, Chg.

Examples of compounds which may be preferably used in the invention include:

Ac-D-βNal-Pro-boroArg pinanediol ester
Z-D-Dpa-Pro-boroIrg pinanediol ester
Z-D-Dpa-Pro-boroPgl pinacol ester
Ac-D-βNal-Pro-boroMbg pinanediol ester
CH$_3$-D-Dpa-Pro-Arg-H
Boc-D-Dpa-Pro-Gpa-H
CH$_3$D-Dpa-Thi-Mbg-H
H-D-Dpa-Pro-Arg-k-Gly-pip
Z-D-Dpa-Pro-Arg-CH$_2$Cl
Boc-D-Dpa-Pro-ArgCN
H-Dpa-Pro-Arg$^P$(OPh)$_2$
H-D-βNal-Pro-Pgl$^P$(OPh)-Gly-pip
H-D-Dpa-Pip-Arg-pNA
H-D-βNal-Pro-Chg-pNA Further examples of compounds which may be preferably used in the invention are those listed in Examples 10 to 22 below.

Inhibition data for some of the new compounds are shown in Tables 1–7. The advantages of replacing Phe by amino acids according to the invention are clearly shown in the Ki values, which are generally 3 to 10 times better for the new compounds, as well as in the prolongation of the thrombin time. The importance of the D-form of the N-terminal amino acid is also evident from Table 1. The drastic reduction of the blood pressure lowering side-effect with compounds according to the invention is shown in Table 2.

TABLE 1

| In-vitroassays | Ki (μM) | TT (μM) | APTT (μM) |
|---|---|---|---|
| D-Phe—Pro—Gpa—k—Gly—Pip | 1.3 | 4.9 | |
| 4  D,L-Dpa—Pro—Arg—k—Gly—Pip | 0.6 | | 45.0 |
| 6  D-Dpa—Pro—Arg—k—Gly—Pip | 0.2 | 0.65 | 8.0 |
| 7  L,Dpa—Pro—Arg—k—Gly—Pip | 1.7 | 7.5 | 100.0 |
| 8  D-Fgl—Pro—Arg—k—Gly—Pip | | 50.0 | |
| 9  D,L-α—Nal—Pro—Arg—k—Gly—Pip | 13.5 | | |
| 14  D,L-β—Nal—Pro—Arg—k—Gly—Pip | 11.6 | 90.0 | |
| 54  D-B—Nal—Pro—Arg—k—Gly—Pip | 2.87 | 5.3 | 45.0 |

TABLE 2

| In-vitroassay | Ki(μM) | TT (μM)* | APTT (μM) | Blood pressure % of normal |
|---|---|---|---|---|
| Boc-D-Phe—Pro—Arg—H | 0.1 | 5 | | 40** |
| Boc-D,L-Dpa—Pro—Arg—H | 0.03 | 3 | | 100** |
| Boc-D,L-Dpa—Pro—Gpa—H | 0.03 | 3 | | nd |
| 33  Z-D-Phe—Pro—Pgl—H | 4.66 | 86.0 | | nd |
| 48  Z-D,L-Dpa—Pro—Pgl—H | 0.071 | | | nd |
| 53  Boc-D-Phe—Pro—His—H | 0.726 | 3.1 | 34.0 | 100*** |

*The concentration needed to double the plasma thrombin time
**4 mg/Kg given i.v. to anaesthetized cats
***1 mg/Kg given i.v. bolus to anaesthetized New Zealand white rabbits, 2 per point
ND = Not determined.

TABLE 3

| | Ki (uM) |
|---|---|
| Boc-D-Phe—Pro—ArgCN | 0.8 |
| Boc-D,L-Dpa    -"- | 0.05 |

TABLE 4

| | In-vitroassay | Ki(μM) | TT(μM) |
|---|---|---|---|
| 15 | Boc-D,L-Dpa—Pro—PglP(OH)$_2$ | 59.0 | |
| 16 | D,L-Dpa—Pro—PglP(OH)$_2$ | 0.223 | |
| 17 | Z-D-Dpa—Pro—PglP(OPh)$_2$ | 8.46 | |
| 18 | D-Dpa—Pro—PglP(OH)$_2$ | 15.1 | |
| 19 | Z-D-Phs—Pro—PglP(OPh)$_2$ | >31.0 | |
| 20 | D-Phe—Pro—PglP(OPh)$_2$ | 0.109 | |
| 21 | D-Phe—Pro—PglP(OH)$_2$ | >98.0 | |
| 23 | D-Dpa—Pro—PglP(OPh) | 0.48 | |
| 32 | H-D-Dpa—Pro—MpgP(OPh)$_2$ | 0.0048 | 9.1 |
| 40 | H-D-Phe—Pro—MpgP(OPh)$_2$ | 0.0188 | |

TABLE 5

| | In-vitroassays | Ki(pM)* | TT(μM) | APTT (μM) |
|---|---|---|---|---|
| 12 | Z-D-Dpa—Pro—BoroIrg—OPin | 368.0 | 0.84 | 1.19 |
| 26 | Z-D-β—Nal—Pro—BoroIrg—OPin | 325.0 | 0.15 | 0.216 |
| 36 | Z-D-Fgl—Pro—BoroIrg—OPin | 1750.0 | 0.643 | 1.23 |
| 37 | Ac-D-Dpa—Pro—BoroIrg—OPin | 2320.0 | | 0.156 |
| 38 | Z-L-Dpa—Pro—BoroIrg—OPin | 4180.0 | 0.26 | 0.239 |
| 46 | Z-D-Cha—Pro—BoroIrg—OPin | 1490.0 | 0.113 | 0.123 |

*Inhibitor Pre-Incubated for 30 min with Thrombin.

TABLE 6

| | In-vitroassays | Ki(nM) | TT(μM) | APTT (μM) |
|---|---|---|---|---|
| 22 | Z-D-Phe—Pro—BoroMbg—OPin | 7.0 | 0.56 | 4.11 |
| 40 | Z-D-Phe—Pro—BoroPhe—OPinac | 12.8 | 0.329 | 2.52 |
| 10 | Z-D-Phe—Pro—BoroAcet—OPinac | 25.0 | 3.4 | 18.2 |
| 11 | Z-D-Phe—Pro—BoroPgl—OPinac | 19.0 | 2.0 | 2.34 |
| 43 | Z-D-Phe—Pro—BoroOct—OPinac | 22.5 | 3.86 | |
| 51 | Z-D-Dpa—Pro—BoroMpg—OPin | 3.4 | 0.629 | 1.96 |
| 59 | Z-D-Phe—Pro—BoroMbg—OPin | 7.43 | 1.12 | 4.0 |

TABLE 7

| | In-vitroassay | Km(μM) |
|---|---|---|
| | H-D-Phe—Pip—Arg—pNA | 10.0 |
| 34 | H-D-β-Nal—Pip—Arg—pNA | 6.9 |
| 35 | H-D,L-Dpa—Pip—Arg—pNA | 9.1 |

Those compounds of the invention which are thrombin inhibitors have anti-thrombogenic properties and may be employed for indications when an anti-thrombogenic agent is indicated. Generally, these compounds may be administered orally or parenterally to a host to obtain an anti-thrombogenic effect. In the case of larger mammals such as humans, the compounds may be administered alone or in combination with pharmaceutical carrier or diluent at a dose of from 0.02 to 15 mg/Kg of body weight and preferably 1–10 mg/Kg to obtain the anti-thrombogenic effect, and may be given as single dose or in divided doses or as a sustained for a patient, 0.1–1 mg/Kg may be administered intravenously. For use with whole blood from 1–10 mg per liter may be provided to prevent coagulation. Pharmaceutical diluents are well known and include sugars, starches and water which may be used to make tablets, capsules, injectable solutions and the like. The compounds of the invention may be added to blood for the purpose of preventing coagulation of the blood in blood collecting or distribution containers, tubing or implantable apparatus which comes in contact with blood.

The advantages of the compounds of the invention include oral activity, rapid onset of activity and low toxicity. In addition, these compounds may have special utility in the treatment of individuals who are hypersensitive to compounds such as heparin.

In the following examples, the symbols have the following meanings:
Aa=amino acid
Ac=acetyl
Boc=t-butyloxycarbonyl
Bu=butyl
Bzl=benzyl
Bzl=Benzyl
DCC=dicyclohexylcarbodiimide
DIEA=diisopropylethylamine
DMAP=4-dimethylaminopyridine
EtOAc=ethyl acetate
EtOH=ethylalcohol
HOSu=N-hydroxy succinimide
MCA=4-methyl-coumaryl-7-amide
MeOH=methylalcohol
Mtr=4-methoxy-2,3,6-trimethylbenzenesulphonyl
NMR=nuclear magnetic resonance
NP=p-nitrophenyl
PinOH=pinanediol
PfpOH=pentafluorophenol
pip=piperidide
pNA=p-nitroanilide
TLC=thin layer chromatography
THF=tetrahydrofuran
TEA=triethylamine
WSC=water soluble carbodiimide
Z=Cbz=benzyloxycarbonyl
Apa=amidinophenylalanine
Chg=cyclohexylglycine
Dpa=3,3-diphenylalanine
Gpa=guanidinophenylalanine
Irg=isothiouronium analogue of Arg
ArgCN=Arg, where COOH is replaced by CN
Mbg=2-(2-methylbutyl) glycine
Nal=naphthylalanine
Pgl=pentylglycine
Thi=thiazolidinecarboxylic acid
boroAa=boronic acid analogue of Aa
Aa$^P$=phosphonic acid analogue of Aa
—k—=amide bond replaced by CO_Ch$_2$ The following non-limiting examples illustrate the preparation of the compounds in this invention.

The synthesis of some of the different inhibitor types are outline in Schemes 1 to 8 and the detailed descriptions are given in the examples below.

HPLC

The following conditions were adopted for the analysis of most of the synthetic compounds on reversed-phase HPLC (RP-HPLC): column; SuperPac Pep-S (4×250 mm), eluant; A=water containing 0.1% TFA, B=acetonitrile containing 0.1% TFA, gradient; 50% to 90% B in A in 25 min, flow rate; 1.0 ml/min, detection; UV absorbance at 210 nm.

TLC

Thin layer chromatography (TLC) was carried out on the following compounds using precoated silica plates (Merck, F254) in the following systems: A, Chloroform-ethyl acetate (2:1); B, chloroform-methanol-acetic acid (20:4:1); C, n-butanol-acetic acid-ethyl acetate-water (1:1:1:1); D, chloroform-methanol (9:1); E, pyridin-ethyl acetate-acetic acid-water (5:5:1:3); F, chloroform-methanol-ammonia (1M) (60:35:5). The spots were visualized by ninhydrin and chlorine-dicarboxidine spray reagents (C. M. Swahn and J. Gyllander, J. Chromatogr. (1970) 170, 292:

NMR spectra

Magnetic resonance spectra were recorded at 250 MHz using a Bruker instrument.

EXAMPLES

1. Synthesis of Dpa, Z-Boc-Dpa-Pro and Z-Dpa-Pro-Arg (Cf. Scheme 1)

(a) DL-Dpa.HCl

To a solution of potassium tertiary butoxide (6.75 g, 0.06 mol) in tertiary butanol (350 ml) was added, at room temperature under argon, ethyl acetamido cyanoacetate (10 g, 0.059 mol). When the solution had become clear bromodiphenyl methane (14.55 g, 0.059 mol) was added. The mixture was stirred at 20° C. for 24 h, then evaporated under reduced pressure. The solid residue was treated with ethyl acetate (500 ml) and water (175 ml). The organic phase was dried ($Na_2SO_4$) and concentrated to give yellow crystals. The crystals were washed repeatedly with ether and dried to give ethyl 2-diphenylmethylacetamido cyanoacetate (11.61 g, 58%, m.p. 181°–185° C.). The ester (11.61 g, 34.4 mol) was mixed with hydrochloric acid (20%) and refluxed for 30 h. The reaction mixture was allowed to cool and the crystals were collected, washed (ether), and dried to give HCl.D,L-Dpa (7.82 g, 81.8%).

(b) Z-DL-Dpa

To a solution of D,L-Dpa.HCl (0.56 g, 0.0021 mol) in NaOH (2N, 5 ml), cooled to 0° C. and vigorously stirred was added, dropwise, benzyl chloroformate (0.39 g, 0.33 ml, 0.0023 mol). The reaction mixture was kept at pH10 and at 5° C. to 10° C. The solution was warmed to room temperature and stirred vigorously for 1 h. The solution was washed with ether (4 times) and acidified to pH3 with HCl (5N). The mixture was extracted with dichloromethane and the organic phase dried and concentrated to give Z-DL-Dpa (0.73 g, 97%,, m.p. 214°–217° C.).

(c) Z-D,L-Dpa-ONSu

To a stirred solution of Z-D,L-Dpa (1.88 g, 0.005 mol) and N-hydroxy succinimide (0.575 g, 0.005 mol) in dry 1,2-dimethoxyethane (30 ml) at 0° C. was added dicyclohexyl carbodiimide (1.03 g, 0.005 mol). The mixture was maintained at 0° C. for 4 h. The suspension was filtered and the filtrate was concentrated to dryness to give an oil which was triturated with ether and filtered to give Z-D,L-Dpa-ONSu (2.15 g, 91%, m.p. 139°–142° C.).

(d) Z-D-Dpa-Pro and Z-L-Dpa-Pro

To a solution of proline (0.78 g, 0.0068 mol) and $NaHCO_3$ (0.57 g, 0.0068 mol) in water (8 ml) was added a solution of Z-D,L-Dpa-ONSu (2.15 g, 0.0045 mol) in 1,2-dimethoxyethane (15 ml). After 2 h the solvent was removed under reduced pressure and water (5 ml) was added. The solution was acidified (conc. HCl) to pH2 to give white crystals (1.98 g, m.p. 113°–117° C.). Fractional recrystallisation from EtOAc gave as the first crop one diastereomer as a solid (0.7 g, m.p. 180°–183° C., FAB MS:$M^+$473; $^1$H nmr: 7.26 (15H, m, 3×Ph), 5.66(1H, d, CH), 5.23 (1H, m, CH), 4.40 (1H, d, CH), 2.03 (2H, s, $CH_2$), 2.20 (4H, m, 2×$CH_2$); $^{13}$C nmr:172.19 (CO), 156.1 (CO), 139.17 (CO), 127–128 (Ph), 66.88 ($CH_2$), 59.48 (CH), 55.58 (CH), 24.15 ($CH_2$). Further crystallisation from the mother liquor gave as a second crop a mixture of diastereomers (0.43 g, m.p. 126°–130° C.). Addition of petroleum ether (b.p. 60°–80° C.) gave the other isomer (0.54 g, m.p. 128°–131° C.), FAB MS:$M^{3o}$473; H nmr: 7.29 (15H, m, 3Ph), 5.55 (1H, d, CH), 5.23 (1H, m, CH), 4.47 (1H, d, CH), 2.04 $CH_2$); $^{13}$C:172.77 (CO), 156.13 (CO), 139.48 (CO), 126.99–128.72 (Ph), 66.90 ($CH_2$), 59.62 (CH), 55.48 (CH), 53.54 (CH), 47.44 ($CH_2$), 27.94 ($CH_2$), 24.58 ($CH_2$).

(e) Z-D-Dpa-Pro-Arg(Mtr)OPh

To a solution of Z-D-Dpa-Pro-OH (0.472 g, 1 mmol) and HOSu (0.115 g, 1 mmol) in dimethoxyethane (20 ml) was added DCC (0.206 g, 1 mmol) with cooling over an ice water bath, the solution was then stirred at r.t. for 3 h, the DCU formed was filtered off and the solution was concentrated to dryness to give an oil (0.57 g). To a solution of H-Arg(Mtr)-OH (0.42 g, 1.1 mmol) and $Et_3N$ (0.12 g, 1.1 mmol) in DMF (25 ml) was added a solution of Z-Dpa-Pro-OSu (0.57 g) in dimethoxyethane (15 ml) with cooling. The solution was stirred at room temperature for 3 h. The solvent was evaporated and the residue was dissolved in $H_2O$ (20 ml) and MeOH (10 ml). The solution was acidified to pH2 and the MeOH was removed under reduced pressure. The solid formed was filtered off and dried to give Z-D-Dpa-Pro-Arg(Mtr)OH (0.766 g, 91%). The structure of the compound was confirmed by $^1$H NMR.

Fgl and Nal and their corresponding di- and tripeptides were synthesized in a manner analogous to the above procedures.

2. Synthesis of peptide aminophosphonic acid inhibitors (Cf. Scheme 3)

(a) Diphenyl 1-(N-benzyloxycarbonyl) aminopentanephosphonate

A mixture of triphenyl phosphite (9.3 g, 30 mmol), n-hexanal (4.50 g, 45 mmol), benzylcarbamate (4.53 g, 30 mmol), glacial acetic acid (5 ml) was stirred for 45 min. The mixture was then heated at 80°–85° C. for 1 h and volatile by-products were removed in vacuo with heating on a boiling water bath. The oily residue was dissolved in methanol (40 ml) and left for crystallization at −10° C. to give 7.28 g, m.p. 70°–72° C., 52% yield. The structure was confirmed by proton NMR.

(b) Diphenyl 1-aminopentanephosphonate

Diphenyl-1-(N-benzyloxycarbonyl) aminopentanephosphonate (0.93 g, 2.0 mmol) was dissolved in ethanol (30 ml) and acetic acid (0.2 ml) was added. Then 10% palladium on charcoal (100 mg) was added and the mixture was hydrogenated for 4 h. The catalyst was filtered off, washed with ethanol (5×5 ml). After removal of the solvent an oil was obtained. The oil was washed with water to remove acetic acid and dissolved in chloroform, dried ($MgSO_4$), concentrated to dryness to give oily product, 0.45 g, 68% yield. The structure was confirmed by proton NMR and MS.

(c) Z-D-Dpa-Pro-Pgl$^P$(OPh)$_2$

Z-D-Dpa-Pro-OH (0.11 g, 0.25 mmol) was dissolved in dry chloroform (2 ml) containing $Et_3N$ (0.035 ml) was cooled to −5° C. Ethyl chloroformate (0.026 ml, 0.275 mmol) was added and the mixture kept at −5° C. for 30 min. A solution of diphenyl 1-aminopentanephosphonate (83 mg, 0.25 mmol) in dry chloroform (2 ml) containing $Et_3N$ (0.025 g, 0.25 mmol) was added. The mixture was stirred at r.t. for 12 h. Solvent was removed in vacuo. The resulting oil was chromatographed ($CHCl_3$ then 2% MeOH in $CHCl_3$) to give 123 mg as crystals, 63% yield. The structure was confirmed by proton and $^{31}$p NMR.

(d) H-D-Dpa-Pro-Pgl$^P$(OPh)$_2$

Z-D-Dpa-Pro-Pgl$^P$(OPh)$_2$ (50 mg, 0.063 mmol) was dissolved in ethanol (5 ml) and acetic acid (0.01 ml) was added. 10% Pd/C (25 mg) was added and the mixture was hydrogenated at r.t. for 3 h. The catalyst was filtered off and ethanol removed in vacuo. The resulting oil was treated with water (5 ml) and chloroform (20 ml). The chloroform phase was dried (MgSO$_4$) and concentrated to dryness to give crystals, 41 mg, 91% yield. The structure was confirmed by $^1$H and $^{31}$P NMR.

(e) H-D-Dpa-Pro-Pgl$^P$(CH)$_2$

Z-D-Dpa-Pro-Pgl$^P$(OPh)$_2$ (100 mg, 0.127 mmol) was dissolved in ethanol (10 ml) and acetic acid (0.1 ml) was added. Then 10% Pd/C (50 mg) was added and the mixture was hydrogenated at r.t. for 3 h. The catalyst was filtered off, PtO$_2$ (100 mg) was added and the mixture was hydrogenated at r.t. for 4 h. The catalyst was filtered off, solvent was removed and the residue was treated with 20 ml of water and chloroform (60 ml). The organic layer was dried (MgSO$_4$), concentrated to dryness to give 67 mg as crystals, 92% as overall yield. The structure was confirmed by $^1$H and $^{31}$P NMR.

Z-D-Phe-Pro-Pgl$^P$(OPh)$_2$

This compound was synthesized by the above procedure in 73% yield. The structure was confirmed by $^1$H and $^{31}$P NMR.

H-D-Phe-Pro-Pgl$^P$(OPh)$_2$

The compound was synthesized by the above procedure in 90% yield. The structure was confirmed by $^1$H and $^{31}$P NMR.

H-D-Phe-Pro-Pgl$^P$(OH)$_2$

The compound was synthesized by the above procedure in 89% overall yield. The structure was confirmed by $^1$H and $^{31}$P NMR.

(f) Diphenyl 1-(N-allyl)amino-4-Pyridylmethyl-phosphonate

To a solution of 4-pyridinecarboxyaldehyde (1.07 g, 10 mmol) and allylamine (0.61 g, 10 mmol) in ether (30 ml) was added anhydrous sodium carbonate (2.76 g). The solution was stirred at r.t. overnight, then sodium carbonate was filtered off. To the reaction mixture, diphenylphosphite (2.34 g, 10 mmol) and triethylamine (1.01 g, 10 mmol) were added with cooling over an ice-water bath. It was stirred at r.t. overnight. After removal of the solvent an oily residue was obtained which was chromatographed (1:1 Petroleum ether/ethyl acetate) to give 2.85 g (65%) as an oil.

(g) Diphenyl 1-(N-allyl)amino-4-(tert-butyloxycarbonyl) butyl-phosphonate 4-(tert-butyloxycarbonyl)amino-butylaldehyde diethyl acetal (2.91 g, 10 mmol) was dissolved in acetone (20 ml) in the presence of 1N hydrogen chloride (1 ml) and PPTS (150 mg). The reaction mixture was refluxed for 3 h. The solvent was removed and the residue was dissolved in chloroform and dried (MgSO$_4$). After removal of MgSO$_4$ the solution was stirred and allylamine (0.61 g, 10 mmol) and anhydrous sodium carbonate (2.76 g) were added. The reaction suspension was stirred at r.t. overnight. The sodium carobonate was filtered off. To the solution obtained, diphenylphosphite (2.34 g, 10 mmol) and the triethylamine (1.01 g, 10 mmol) were added. It was stirred at r.t. for 2 days. The residue obtained after evaporation was chromatographed on silica gel (1:1 Petroleum/ethyl acetate) to give 200 mg as a yellow waxy solid (5%).

(h) Diphenyl 1-amino-4-pyridyl-methyl-phosphonate

The N-allyl protected compound (1.0 g, 2.3 mmol) was dissolved in ethanol (25 ml). To the solution was added 10% Pd/C (300 mg) that it was refluxed for 20 hours. The reaction was followed by HPLC, retention time; 10.0 min for the product and 12.0 min for the starting material. After removal of the solvent the product was obtained by chromatography, 0.51 g (56%) as a yellow oil.

The following tripeptides were synthesized according to Scheme 5:
Z-D-Phe-Pro-Cpg$^P$(OPh)$_2$:0.36 g(67%)
Z-D-Phe-Pro-Epg$^P$(OPh)$_2$:0.31 g(87%)
Z-D-Phe-Pro-Pyg$^P$(OPh)$_2$:0.41 g(35%)
Z-D-Phe-Pro-Dmg$^P$(OPh)$_2$:0.25 g(70%)
Z-D-β-Nal-Pro-Mpg$^P$(OPh)$_2$:54 mg(32%)
H-D-Phe-Pro-Epg$^P$(OPh)$_2$:126 mg(71%)
H-D-Phe-Pro-Dmg$^P$(OPh)$_2$:85 mg(52%)

Abbreviations:
Mpg=methoxypropylglycine
Cpg=4-cyanophenylglycine
Epg=2-ethylpropylglycine
Pyg=4-pyridylglycine
Dmg=3,3-dimethylpropylglycine
Nal=naphtylalanine
PPTS=Pyridinium p-toluenesulfonate 3. Synthesis of peptide aminoboronic acid inhibitors (a) (+)-Pinanediol 4-bromo-R-1-aminobutane boronate hydrochloride The title compound was prepared as described by D. S. Matteson et al (1984) in Organometallics, 3, 1284–1288 and in European patent appl. 293881A2.

(b) Z-D-Dpa-Pro-Irg-OPin.HCl

To a solution of Z-D-Dpa-Pro-OH (236 mg, 0.5 mmol) in THF (5 ml) in the presence of trieethylamine (70 μl, 0.5 mmol) was added isobutyl chloroformate (65 μl, 0.5 mmol) at −15° C. and the solution was stirred at −13° C. for 13 min. After the addition of (+)-pinanediol 4-bromo-R-1-aminobutaneboronate hydrochloride (183 mg, 0.5 mmol) in CHCl$_3$ followed by that of Et$_3$N (70 μl, 0.5 mmol), the reaction mixture was stirred at the same temperature for 2 h, and then below 10° C. for 2 h. THF was removed under reduced pressure and the residue was dissolved in ethyl acetate (50 ml), which was washed with 1% NaHCO$_3$, water, 0.2N HCl and water, and then dried over Na$_2$SO$_4$. Removal of solvent gave an oily product quantitatively. HPLC analysis showed one major peak at the retention time of 22.8 min along with several minor components.

To a solution of the above compound (⅔th of total amount synthesized, 0.2 mmol) in ethanol (1 ml) was added chiourea (61 mg, 0.8 mmol) under an atmosphere of argon at room temperature. After stirring for 4 days, ethyl acetate (70 ml) was added to the reaction mixture, which was washed with 1% NaHCO$_3$, water, 0.2N HCl and then water, and dried over Na$_2$SO$_4$. The residue obtained by removing the solvent was treated with n-hexane to get the product as a powder. Reprecipitation from ethyl acetate with 2:1 mixture of ethyl ether and n-hexane gave a product (98.8 mg, 60.6%, two step overall). Retention time on RP-HPLC analysis was 13.5 min under the conditions described at the general procedure. $^1$H NMR analysis is deuterated chloroform gave a complex pattern because of the existence of proline of proline residue in the molecule, however, the typical signals corresponding to pinanedioil were observed as proper ratios.

4. Z-D-Phe-Pro-boroMbg-OPin (Cf. Scheme 4)

A solution of pinanediol (dichloromethyl)boronate (1 ml, 1.2 g, 4.6 mmol) in THF (7 ml) was placed in a septum fitted flask (100 ml), and 1,1-dimethylpropane magnesium chloride (4.6 ml, 4.6 mmol) added dropwise from a dry syringe at 0° C.

The reaction mixture was left stirring under nitrogen at room temperature. After 7 hours TLC showed mainly one spot [Rf=0.82, chloroform:pet.ether (1:1)]. The solvent was removed and the residue dissolved in ether (50 ml), washed with water (2×10 ml), dried (MgSO$_4$) and filtered.

The ether was removed and the crude product purified on a column of silica gel, eluted with hexane and 10% of chloroform to give α-chloroboronic ester as a pale yellow oil (0.55 g, 40% yield).

The above compound (0.55 g, 1.8 mmol) in THF (5 ml) was added via a double ended needle at −78° C. to a solution of lithiumbis(trimethyl-silyl) amide (1.8 ml, 1.8 mmol) in THF (5 ml) under nitrogen. The reaction mixture was kept overnight at 20° C. then the solvent was removed. The crude product was dissolved in petroleum ether (40°–60° C.) (25 ml) to precipiate out the inorganic salt (LiCl). The reaction mixture was filtered, cooled to −78° C. and dry etheral HCl, 1M (3 equiv, 5.4 mmol) added. The flask was kept in a fridge overnight. Next morning, the reaction mixture was filtered to isolate the hydrochloride (0.41 g, 1.29 mmol, 72% yield) as a white solid.

Z-D-Phe-Pro-OH (0.45 g, 1.1 mmol) was dissolved in THF (7 ml) and the equivalent of N-methylmorpholine (0.11 g, 1.1 mmol) added. The solution was cooled to −20° C. and one equivalent of isobutylchloroformate (0.148 g, 1.1 mmol) added dropwise. After 10 min., a solution of the above aminohydrochloride (0.348 g, 1.1 mmol) dissolved in THF (7 ml) was transferred under nitrogen, and triethylamine (0.11 g, 1.1 mmol) added to the reaction mixture. The reaction mixture was stirred for one hour at −20° C., followed by 2 h at room temperature. Insoluble material was removed by filtration, then the solvent removed by evaporation, and the residue dissolved in ethyl acetate (30 ml). The organic layer was washed with 0.2N hydrochloric acid (10 ml), 5% aqueous sodium bicarbonate, saturated solution of sodium chloride and water. The organic phase was then dried over anhydrous MgSO$_4$, filtered and the solvent evaporated to give a white solid which was purified on a column of silica get eluted with light petroleum to give the desired product (0.59 g, 81%). The structure was confirmed by $^1$H NMR and MS.

5. PREPARATION OF α-BROMO BORONIC ESTERS (Cf. Scheme 6)

All the reactions involving boron used purified anhydrous reagents.

Reactions were carried out under argon or nitrogen used directly from the cylinder through a glass line.

In a 250 ml reaction flask fitted with a reflux condenser was placed 1-bromo-1-propene (3.63 g, 30 mmol).

Dibromo borane -methyl sulfide complex in dichloromethane (60 ml, 60 mmol) was then added to the reaction flask dropwise and the mixture was refluxed under nitrogen for 5 h.

The solvent was removed and the reaction mixture washed with water and dried (MgSO$_4$).

A dry round-bottomed flask (100 ml) was charged with the bromo boronic acid (0.5 g, 3 mmol) and pinanediol (0.52 g, 3 mmol) a magnetic follower and dry ether (20 ml), fitted with a septum and flashed with nitrogen.

The reaction mixture was left stirring for two hours until the solid dissolved, the organic phase was washed with water (10 ml), separated, dried (MgSO$_4$) and filtered. The crude product was purified on a column of silica gel (230–400 mesh), eluted with chloroform (the product was eluted before the pale red ring). The first fraction (100 ml) was collected and the solvent evaporated to give α-bromo boronic ester (0.8 g, 88.6%) as a colourless liquid.

6. Synthesis of isosteric ketomethylene inhibitors (Cf. Scheme 2)

(a) Boc-D-Dpa-Pro-Arg(Mtr)-k-GlyOMe (modified Darkin-West reaction)

Boc-D-Dpa-Pro-Arg(Mtr)-OH (0.126 g, 0.15 mmol) was added to monomethylsuccinyl anhydride (0.259 g, 1.0 mmol). Et$_3$N (0.042 ml, 0.30 mmol), DMAP (1.8 mg, 0.015 mmol) and pyridine (0.12 ml) were added, the reaction flask was fitted with a reflux condenser, and the reaction was heated at 45°–50° C. The reaction mixture was stirred for 1 h, then NaHCO$_3$ (5%, 5 ml) was added and the stirring was continued for an additional 30 min. The product was extracted into ethyl acetate and washed with AcOH (0.1N) and brine. The organic layer was dried (MgSO$_4$), filtered and concentrated to dryness to give an oily residue which was chromatographed on silica gel (grade 9385, 50 g). Elution with CHCl$_2$:CH$_3$OH,98:2 gave the product after removal of the solvent as a brown oil (0.134 g, 98%). The structure was confirmed as Boc-Dpa-Pro-Arg(Mtr)-k-GlyOMe by $^1$H NMR (250 MHz), and by FAB mass spectrometry.

(b) Z-D-Dpa-Pro-Arg(Mtr)-k-Gly-pip

A solution of Z-D-Dpa-Pro-Arg(Mtr)-k-Gly-OMe (0.1 g, 0.1 mmol) in MeOH (10 ml) was cooled to 0° C. and NaOH (1N, 0.22 ml, 0.22 mmol) was added with stirring for 2.5 h at room temperature. The solution was neutralized to pH7 and the MeOH was removed under reduced pressure. The aqueous solution was acidified (pH2) and extracted by ethyl acetate and dried (Na$_2$SO$_4$). The solvent was removed under reduced pressure to give an oil. To a solution of the oil and HOSu (12 mg, 0.1 mmol) in dimethoxy ethane (20 ml) was added DCC (21 mg, 0.1 mmol), with cooling. The solution was stirred at room temperature for 20 h, and piperidine (17 mg, 0.2 mmol) was added to the solution with cooling and the solution was stirred at room temperature for a further 3 h. The solution was concentrated to dryness and the product was purified by chromatography on silica gel (MeOH:CHCl$_3$, 92:2) to give Z-D-Dpa-Pro-Arg(Mtr)-k-Gly-pip (78 mg, 81%). The structure of the product was confirmed by $^1$H NMR and FAB mass spectrometry.

In a separate experiment the L-isomer Z-L-Dpa-Pro-Arg(Mtr)-k-Gly-pip, was synthesized by the above procedure in 55% yield.

(c) H-D-Dpa-Pro-Arg-k-Gly-pip.2TFA

Z-D-Dpa-Pro-ArgMtr-k-Gly-pip (52 mg, 0.053 mmol) was dissolved in 0.9 ml of TFA and 0.1 ml of thioanisole at room temperature. After stirring for 4 h. TFA was removed at reduced pressure and the residue was triturated with ether. The crystals were collected and washed with ether (52 mg of Mtr deprotected product). The crystals were then dissolved in 5 ml of methanol and 21 mg of 10% Pd/C was added. After 20 h. hydrogenation at room temperature the catalyst was removed by filtration and the solvent evaporated. The residue was triturated with ether to give white crystals. 34 mg (75%), m.p. 146–151 (dec.). HPLC showed two equally big peaks, from the two forms containing D and L Arg. The structure was confirmed by $^1$H NMR and FAB mass spectrometry.

In a separate experiment the L-isomer of Z-Dpa-Pro-Arg(Mtr)-k-Gly-pip was deprotected to give H-L-Dpa-Pro-Arg-k-Gly-pip.2TFA in 43% yield.

7. Synthesis of peptide aldehydes (Cf. Scheme 8)

(a) Z(NO$_2$)Arg NCH$_3$(OCH$_3$)

N,O-dimethylhydroxylamine hydrochloride (1.45 g, 14.9 mmol) was dissolved in 10 ml of DMF, and the solution kept at 0° C. Diisopropylethylamine (1.92 g, 14.9 mmol) was first added and then Z-(NO₂)Arg in 10 ml of DMF, HOBT (1.92 g, 14.2 mmol) and WSC.HCL (2.99 g, 15.6 mmol). After 5 h reaction 0° C. the solution was left at room temperature overnight. The solvent was removed at reduced pressure and 100 ml of EtOAc and 25 ml of H₂O were added. The organic phase was diluted with ether and washed with Na₂CO₃ (0.5M), H₂O, H₂SO₄ (0.1M) and H₂O, then dried and the solvents removed giving 3.66 g of product. The water solutions were combined, extracted and treated in the same way as above giving further 1.69 g. Totally 5.35 g (95%) which was chromatographed on Sephadex LH-20 with 95% ethanol. Yield 4.60 g (82%) of homogenous product (TLC in S₁ and S₂). NMR confirmed the structure.

(b) Arg(NO₂)—NCH₃(OCH₃).HBr

The above compound was deprotected in HBr/HOAc at room temperature for 45 min in the usual manner. The product was homogeneous according to TLC in S₃, S₄ and S₅.

(c) Boc-D,L-Dpa-Pro-Arg(NO₂)—NCH₃(OCH₃)

Arg(NO₂)—NCH₃(OCH₃).HBr (4.9 g, 13 mmol) was dissolved in DMF, the solution cooled to −5° C. and Et₃N added to alkaline reaction. Boc-DL-Dpa-Pro OH (5.5 g, 12.5 mmol), HOBT (1.7 g, 12.5 mmol) and WSC (2.8 g, 14.5 mmol) were added and the reaction mixture stirred for 2 h, at −5° C. and then stirred at room temperature overnight. The solvent was evaporated at reduced pressure. EtOAc and H₂O were added, the organic phase separated and extracted with 0.5M NaHCO₃ (3×30 ml), NaCl solution (4×20 ml), dried (NaSO₄) and the solvent removed. Yield 8.3 g (97%) TLC (S₂) shows one spot. The expected structure of the compound was confirmed with NMR.

(d) Boc-D,L-Dpa-Pro-Arg-NCH₃(OCH₃).HCl

The above compound (2.33 g, 3.4 mmol) was dissolved in 240 ml of MeOH and 3.6 ml HCl (1M). The catalyst, 10% Pd/C (0.6 g) was added and hydrogenation performed at room temperature for 20 h. The catalyst was filtered and the solvent removed at reduced pressure. Remaining 2.3 g solid contained some starting material which was removed by ion exchange chromatography on Sephadex QAE⁺Cl⁻ with 50% EtOH. Yield 1.74 g (76%). TLC (S₂ and S₃) showed a single spot.

(e) Boc-D,L-Dpa-Pro-Arg-H.HCl

The above compound (0.5 g, 0.74 mmol) was dissolved in 40 mol of dried (molecular sieve, 4A) THF and the solution was cooled to −40° C. and 3.2 ml of DIBAH (1M toluene solution, 3.2 mmol) was added dropwise during stirring in argon atmosphere. After 3 h, 12.8 ml of 0.25M citric acid was added. The aluminium salts were centrifuged and washed several times with THF/H₂O (4:1). From the combined liquid phases THF was removed at reduced pressure and the product extracted with EtOAc. The solvent was removed, the product dissolved in 15 ml of 20% HOAc and chromatographed on Sephadex G15 with 20% HOAc as eluent. Yield 172 mg (38%). The compound shows a double spot in TLC (S₂ and S₃) probably showing the two isomeres with D- and L-Dpa, respectively. NMR and MS were in agreement with the expected structure.

8. Synthesis of Boc-D,L-Dpa-Pro-ArgCN.HCl (a) Z-D,L-Dpa-Pro-Arg-NH₂.HCL

Arg-NH₂.2HCl and Boc-D-L-Dpa-ProOH were coupled in the normal way with HOBT and DCC in DMF. Yield 53%.

(b) Boc-D,L-Dpa-Pro-ArgCN.HCl

The above tripeptide amide (0.50 g, 0.79 mmol) and tosylchloride (0.50 g, 2.55 mmol) were dissolved in 2 ml of pyridine at room temperature and stirred for 24 h. The pyridine was evaporated at reduced pressure. 5 ml of pyridine and 0.5 ml of water were then added and stirring continued for 2 h. After evaporation at reduced pressure the residue was triturated with a small amount of water, dissolved at EtOAc, dried (Na₂SO₄) and chromatographed on Sephadex QAE⊕ Cl⊖. The fractions containing the product were evaporated, dissolved in 10% HOAc and freeze dried. Yield:0.33 g (68%). [α]D²²°=−144° (C=0.5, 50% HOAc). The structure was confirmed with ¹H NMR and mass spectroscopy.

9. Synthesis of Dba (a) Preparation of N-formyl-N,α,β-tribenzylalanine cyclohexylamide Bzl-NH₂ 288 µl (2.64 mmol) and benzyl phenethylketone 592 mg (2.64 mmol) were dissolved in MeOH (5 ml) at rt and the solution was stirred overnight. To the mixture were added formic acid 99.6 µl (2.64 mmol) and cyclohexyliso-cyanide 298 µl (2.4 mmol) at rt, which was allowed to react at rt for 2 weeks. Insoluble material in MeOH was collected by filtration and washed with MeOH, ether and then n-hexane. The crude product was recrystallized from CHCl₃ with the 2 to 1 mixture of ether and n-hexane. Yield 540 mg (48.2%). NMR in CDCl₃; δ=0.8–1.8 cyclohexyl (11H), δ=2.1–4.75 CH₂ (8H), δ=5.45–5.55 NH (1H), δ=7.0–7.4 phenyl (15H), δ=8.25 (main) and 8.4 (minor) formyl (1H).

(b) Preparation of Bzl-Dba

The fully protected Dba 400 mg (0.85 mmol) was dissolved in 2.5 ml of TFA and 3 ml of 11N HCl and the solution was kept at 145° C. with water-cooled condenser and stirred for 20 h. After removal of TFA, the pH of the solution was adjusted around 7 by addition of 10N NaOH. Further addition of ether gave a powder which was collected and washed with ether. Yield 124 mg (40.4%).

10. Synthesis of Z-D-Phe-Pro-Pgl-H (a) Pgl

Pentylglycine was obtained by the Strecker* synthesis, using hexanal, in a yield of 31.6%.

(*Vogel, Textbook of Practical Organic Chemistry)

(b) Z-Pgl

To a solution of pentylglycine (0.5 g, 3.5 mmol) in a mixture of water (4 ml) and THF (4 ml) to give a 0.5M solution, in the presence of triethylamine (0.64 ml, 1.22 eq.) was added Z-OSu (0.963 g, 3.86 mmol.) at room temperature, solution became clear after 15 min. TLC after 2 h indicated some starting material and so a further portion of triethylamine (0.2 ml) and Z-OSu (200 mg) was added. TLC after a further 2 h indicated no starting material and so the solution was poured onto water (50 ml) and was extracted by CHCl₃(50 ml). The organic phase was washed by HCl (1M, 20 ml) and dried (MgSO₄) and concentrated to give Z-Pgl (1.18 g) as a gummy solid, which was recrystallised (DCM/Petroleum ether bp60°–80° C.) to a white crystalline solid (0.8 g). Structure was confirmed by ¹H Nmr.

(c) Z-Pgl-NMe(OMe)

To a solution of hydroxylamine (184 mg, 1.05 eq.) was added DIPEA (0.33 ml, 1.05 eq.), and after 5 min a solution of Z-Pgl (0.5 g, 1.8 mmol) the HOBT (0.242 mg, 1 eq.). The solution was cooled to −15° C. and a solution of WSCI.HCl (0.378 mg, 1.1 eq.) was added. The solution was maintained at −15° C. for 30 min. then allowed to warm to room temperature and pH adjusted to ~pH4 by addition of acetic acid. TLC after 16 h shows little starting material and so the solution was poured onto NaHCO₃ (100 ml) and extracted by Et$_2$O (50 ml). The Et$_2$O phase was washed by NaCl (20 ml). The aqueous phase was washed by Et$_2$O, the organic phases were combined and then concentrated to give Z-PglNMe(OMe) (324 mg). Structure confirmed by $^1$H Nmr and mass spec.

(d) PglNMe(OMe)

To a solution of Z-PglNMe(OMe) (324 mg) in MeOH (10 ml) was applied a vacuum, then argon. Purging was repeated twice, but on the third time Pd/C (~0.5 g) was added. Purging was repeated twice more and on the third time the vacuum was quenched by bubbling Hydrogen through the solution. AcOH (0.5 ml) was the added. After 90 min TLC indicated no starting material and so the solution was filtered (celite), washing with a large volume of MeOH, and concentrated to give PglNMe(OMe)(380 mg), as a gum. Structure was confirmed by $^1$H Nmr.

(e) Z-D-PheProPglNMe(OMe)

To a solution of Z-D-PhePro (0.187 mg, 1 eq.) in DMF (2 ml) was added DIPEA (0.084 ml, 1 eq.) and PyBOP (0.25 mg, 1 eq.), with stirring under argon. After 10 min a solution of PglNMe(OMe) (0.09 mg, 0.479 mmol), in DMF (1 ml), was added. After 90 min TLC indicated no starting material and so the solution was poured onto HCl (1N, 50 ml) and extracted by Et$_2$O (50 ml). The Et$_2$O layer was washed by NaHCO$_3$ (50 ml, 1.2N) and NaCl (sat'd, 20 ml) and dried (MgSO$_4$). Repeated chromatography on silica gel (Merck 9385), eluting with CHCl$_3$/MeOH gave Z-D-Phe-Pro-PglNMe(OMe) (200 mg). Fab Ms shows 567 (10%, M+H), and 589 (100%, M+Na) as required, the structure was also confirmed by $^1$H Nmr.

(f) Z-D-Phe-Pro-Pgl-H

To a solution of Z-D-PheProPglNMe(OMe) (33 mg) in THF (2 ml) at –40° C. was added Di-isobutylaluminium hydride (1N, 0.155 ml, 2.5 eq.), under argon. The solution was allowed to warm to room temperature and stirred for 18 h. TLC showed no starting material and so was quenched by H$_2$SO$_4$ (1N, 0.5 ml) and stirred for 10 min. The aqueous phase was then extracted by EtOAc (20 ml). the organic phase was dried (MgSO$_4$) and concentrated to give Z-D-PheProPgl-H (31 mg). The structure was confirmed by $^1$H Nmr and mass spectrum, and the compound was sent for biological testing, as compound number 33.

11. Z-L-Val-pNa 4-nitroaniline (67.5 g, 0.48 mol) was dissolved in pyridine (dried over 4A sieves, 750 ml), and the solution was cooled down with ice. PCl$_3$ (34.3 g, 0.25 mol) was dissolved in pyridine (350 ml) and added dropwise to the nitroaniline solution. The solution was allowed to stand for 30 min. at room temperature. To the solution was added a solution of ZZVal-OH (112 g, 0.44 mol) in pyrridine (250 ml). The reaction mixture was stirred at room temperature for 1 week, then the pyridine was removed on a rotavapor. The residue was treated with NaHCO$_3$ (2%). The product crystallized was dissolved in boiling EtOH (2000 ml, 95%) and the hot solution was filtered and left to stand overnight at room temperature. The crystals were filtered giving Z-L-Val-pNA (116.9 g, 71.6%).

12. (a) Boc-Dpa

Boc-Dpa was obtained in an analogous manner to the procedure of Examples 1(*a*) and (*b*).

(b) Boc-Dpa-Pip-Arg-pNA (Cf. Scheme 7)

To a solution of Boc-Dpa.HCl (150 mg, 0.396 mmol) in DMF(5 ml) was added TBTU (133.5 mg, 0.416 mmol, 1.05 eq.) and DIPEA (0.069 ml, 0.396 mmol, 1 eq.), to give a solution of basic pH. PipArgpNA.TFA (238 mg, 0.396 mmol, 1 eq.), was then added. pH of the solution was acidic so a further portion of DIPEA (0.05 ml) was added. After stirring for 16 h, TLC showed a little starting material and so a further portion of DIPEA was added (0.034 ml, 0.5 eq.). TLC after a further 3 h showed no starting material and so the solution was poured onto EtOAc (50 ml) and washed HCl(0.5N, 200 ml), dried (MgSO$_4$) and concentrated to give 430 mg of gum. Trituration with Et$_2$ and petroleum ether (b.p. 60°–°80° C.), over 5 minutes, gave a powder which was filtered, avoiding drying in the air, to give a BocDpa-PipArgpNA.TFA as a powder, 207 mg, 62% yield, Rf 20 min on Rp HPLC (pep-S, 35–70% MeCN+0.1%TFA, 25 min, 1 ml/min.).

(c) Dpa-Pip-Arg-pNA

To solid BocDpaPipArgpNA (100 mg, 0.119 mmol), was added TFA (2 ml), with cooling in an ice bath for 10 min. The ice bath was then removed and the solution stirred for a further 10 min. TLC indicated no starting material, so the solution was concentrated under vacuum (oil pump). Washing with Et$_2$O(150 ml), until the filtrate was neutral pH, gave a powder dried under vacuum to DpaPipArgpNA.2TFA, 92 mg, (90%), as a powder, of retention time (15.5 min on Rp HPLC pep-s, 4×250 mm, 35–70% MeCN +0.1% TFA).

(d) Boc-D-Nal-Pip-Arg-pNA

To a solution of Boc- -D-Nal(150 mg, 0.474 mmol) in DMF (5 ml) was added TBTU (164 mg, 0.51 mmol, 1.05 eq.) and DIPEA (0.083 ml, 0.474 mol), 1 eq.). PipArgpNA.TFA (295 mg, 0.474 mmol, 1 eq.) was then added. After 30 min TLC, using the Sakaguchi reagent (8-hydroxyquinoline, Br$_2$, NaOH), indicated mainly starting material, and so DIPEA (0.083 ml, 1 eq.) was added. After 30 min. TLC indicated mainly starting material and so the reaction was diluted by EtOAc (50 ml) and washed by HCl (0.5N, 100 ml). The organic phase was dried (MgSO$_4$), and concentrated to give an oil (490 mg). Recrystallization from CHCl$_3$/petroleum ether bp 60°–80° C./Et$_2$O gave 90 mg, 20.1% yield, of Boc-Dpa-PipArgpNA.TFA as a powder.

(e) H-D-NalPipArgpNA.2TFA

To solid Boc- -D-NalPipArgpNa.TFA (50 mg, 0.055 mmol), cooled in an ice bath, was added TFA (2 ml), with stirring. After 10 min the ice bath was removed, TLC after 30 min still showed some starting material and so solution was stirred for a further 10 min, then concentrated (oil pump). Trituration with Et$_2$O have a powder. The powder was washed with Et$_2$O, until the eluant was neutral, dried overnight at room temperature to give H-D-NalPipArgpNA as a powder, 42 mg, 92% yield. Retention time 11.5 min on Rp HPLC.

EXAMPLE 13

The following compounds were prepared by the route substantially as outlined in Examples 2*a* to 2*e*:

|    |                                      | Yield        | Physical data to confirm structure |
|----|--------------------------------------|--------------|------------------------------------|
| 15 | Boc-D,L-Dpa—Pro—Pgl$^P$(OH)$_2$      | 96%          | Nmr, Ms.                           |
| 16 | D,L-Dpa—Pro—Pgl$^P$(OH)$_2$          |              |                                    |
| 17 | Z-D-Dpa—Pro—Pgl$^P$(OPh)$_2$         |              |                                    |
| 18 | D-Dpa—Pro—Pgl$^P$(OH)$_2$            |              |                                    |
| 19 | Z-D-Phe—Pro—Pgl$^P$(OPh)$_2$         | 92%          | Nmr, FABMs[M + H]502, m.p. 130–133. |
| 20 | D-Phe—Pro—Pgl$^P$(OPh)$_2$           | 35%          | Nmr, FABMs.                        |
| 21 | D-Phe—Pro—Pgl$^P$(OH)$_2$            |              |                                    |
| 23 | D-Dpa—Pro—Pgl$^P$(OPh)$_2$           |              |                                    |
| 32 | H-D-Dpa—Pro—Mpg$^P$(OPh)$_2$         |              | H, $^{31}$PNmr, HPLC.              |
| 40 | H-D-Phe—Pro—Mpg$^P$(OPh)$_2$         |              | HPLC.                              |
| 55 | H-D-Phe—Pro—Apg$^P$(OPh)$_2$         |              | HPLC.                              |
| 56 | H-D-Phe—Pro—Epg$^P$(OPh)$_2$         | 71%          |                                    |
| 57 | H-D-Phe—Pro—DPg$^P$(Oph)$_2$         | 52%          | Nmr.                               |

EXAMPLE 14

The following compounds were synthesised according substantially to Examples 2a to 2d:

| Z-D-Phe—Pro—Epg$^P$(OPh)$_2$      | 87% |
|-----------------------------------|-----|
| Z-D-Phe—Pro—Cpg$^P$(OPh)$_2$      | 67% |
| Z-D—Phe-Pro—Pyg$^P$(OPh)$_2$      | 35% |
| Z-D-β—Nal—Pro—Mpg$^P$(OPh)$_2$    | 32% |

EXAMPLE 15

The following compound was synthesised according to Examples 2a and 2b:
Mty$^P$(OPh)$_2$

EXAMPLE 16

The following compounds were synthesised according substantially to Example 2f:

D-Phe-Pro-Pyg$^P$(OPh)$_2$
D-Phe-Pro-Aeg$^P$(Boc)(OPh)$_2$
D-Phe-Pro-Npg$^P$(OPh)$_2$

EXAMPLE 17

The following compounds were synthesised according substantially to Examples 6a to 6c:

| 4  | D,L-Dpa—Pro—Arg——k——Gly—Pip       |       |                              |
|----|-----------------------------------|-------|------------------------------|
| 5  | D-Phe—Pro—Gpa——k——Gly—Pip         | 81.21 | Nmr, FABMs, m.p. 110–114.    |
| 6  | D-Dpa—Pro—Arg——k——Gly—Pip         | 74.5% | Nmr, FABMs, m.p. 146–151.    |
| 7  | L-Dpa—Pro—Arg——k——Gly—Pip         | 42.7% | Nmr, FABMs, m.p. 136–140.    |
| 8  | D-Fgl—Pro—Arg——k——Gly—Pip         | 81.3% | Nmr, FABMs.                  |
| 9  | D,L-α—Nal—Pro—Arg——k——Gly—Pip     | 81%   | Nmr, FABMs, m.p. 123–127.    |
| 14 | D,L-β—Nal—Pro—Arg——k——Gly—Pip     | 554   | FABMS.                       |
| 54 | D—β—Nal—Pro—Arg——k——Gly—Pip       | 414   | FABMS.                       |

EXAMPLE 18

The following compounds were synthesised according substantially to Example 10:

| 33 | Z-D-Phe—Pro—Pgl—H              | 99.0%        | Nmr, Fabms[M + H]508, 7%   |
| 48 | Z-D-Dpa—Pro—Pgl—H              | quantitative | Nmr, FabMs[M + H]584, 35%  |
| 53 | Boc-D-Phe—Pro—His—H            | 90%          | Nmr, FabMs[M + H]48%       |
|    | Z-N—Me—Phe—Pro—Pgl—NMe(OMe)    |              |                            |

EXAMPLE 19

The following compounds were synthesised according substantially to Example 11:

| 34 | H-D-β—Nal—Pip—Arg—pNA | 90.6% | Nmr |
|---|---|---|---|
| 35 | H-D,L-Dpa—Pip—Arg—pNA | 81% | Nmr |
|  | H-D-Phe—Pro—Phe—pNA |  |  |

EXAMPLE 20

The following compounds were synthesised according substantially to Example 4:

| 22 | Z-D-Phe—Pro—BoroMbg—OPin | 89% | Nmr |
|---|---|---|---|
| 41 | Z-D-Phe—Pro—BoroPhe—OPinac | 68.6% | Nmr |
| 59 | Z-D-Phe—Pro—BoroMbg—OPin | 90% | Nmr |

EXAMPLE 21

The following compounds were synthesised according substantially to Example 3a:

| 10 | Z-D-Phe—Pro—BoroAcet—OPinac | 42% | Nmr |
|---|---|---|---|
| 11 | Z-D-Phe—Pro—BoroPgl—OPinac | 41.5* | Nmr |
| 39 | Z-D-Dpa—Pro—BoroMpg—OPin |  | Nmr |
| 43 | Z-D-Phe—Pro—BoroOct—OPinac | 774 | Nmr |
| 51 | Z-D-Dpa—Pro—BoroMpg—OPin | quantitative | Nmr |

EXAMPLE 22

The following compounds were synthesised according substantially to Examples 3a and 3b:

| 12 | Z-D-Dpa—Pro—BoroIrg—OPin | 61% | Nmr, FABMs[M]780, 13%. |
|---|---|---|---|
| 26 | Z-D-β—Nal—Pro—BoroIrg—OPin | 41.8% | Nmr, FABMs[M + H]755, 10%. |
| 36 | Z-D-Fgl—Pro—BoroIrg—OPin | 49% | Nmr, FABMs[M + H]778, 11%. |
| 37 | Ac-D-Dpa—Pro—BoroIrg—OPin | 8.1% | Nmr, FABMs[M + H]689, 14%. |
| 38 | Z-L-Dpa—Pro—BoroIrg—OPin | 39% | Nmr, FABMs[M + H]781, 12%. |
| 46 | Z-D-Cha—Prb—BoroIrg—OPin | 41% | Nmr, FABMs[M + H]711, 10%. |

Scheme 1.

Synthesis of the amino acids Dpa, Nal and Fgl and their di- and tripeptides with Pro and Pro-Ara

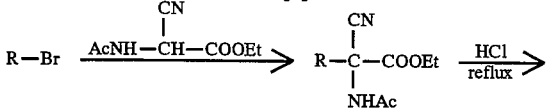

Scheme 1.

Synthesis of the amino acids Dpa, Nal and Fgl and their di- and tripeptides with Pro and Pro-Ara

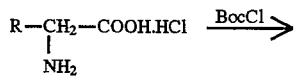

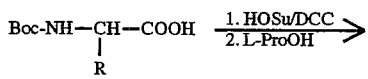

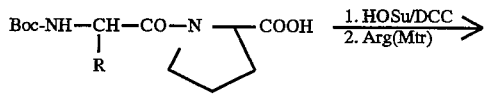

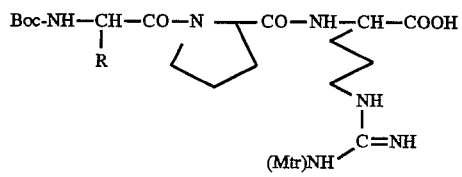

R =

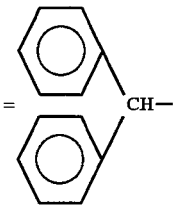

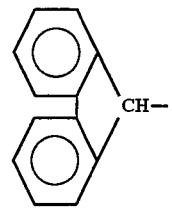

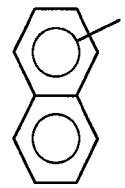

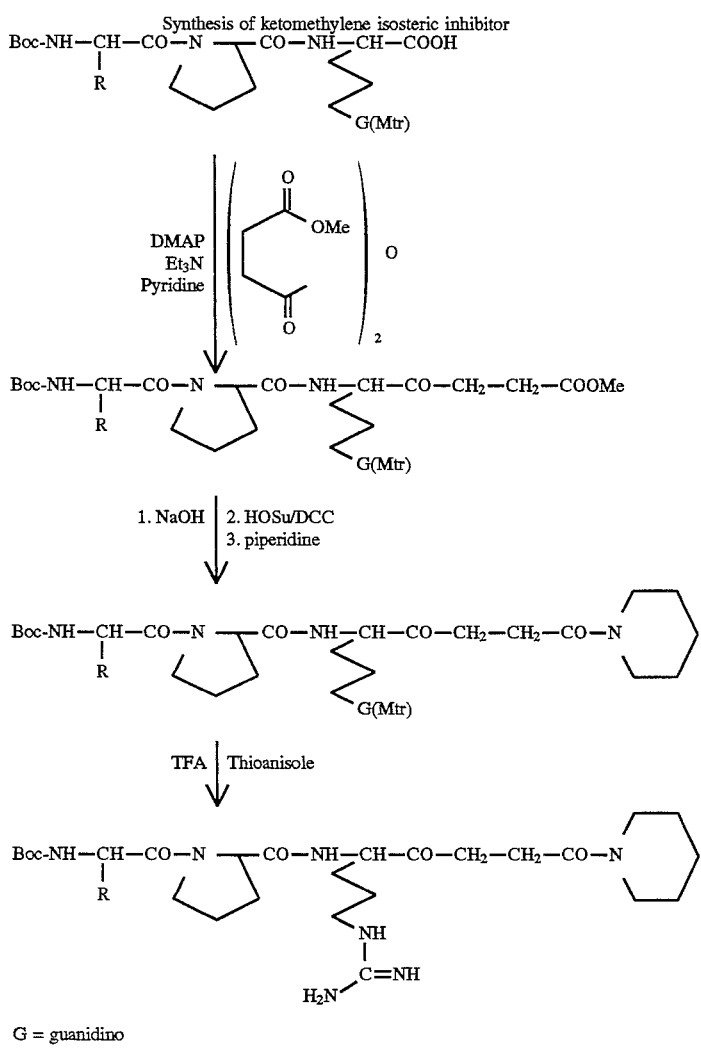
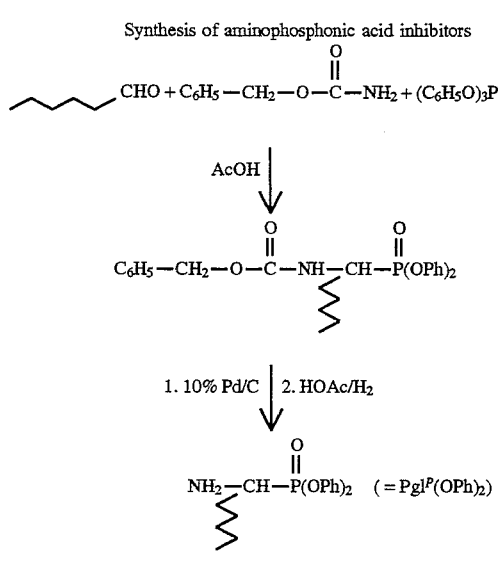
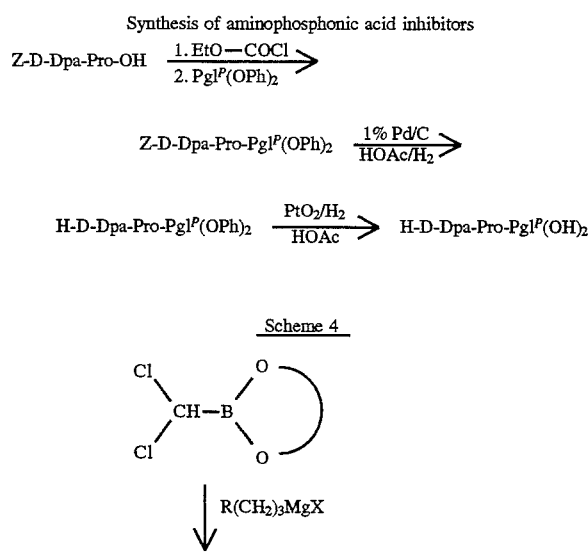

Scheme 4
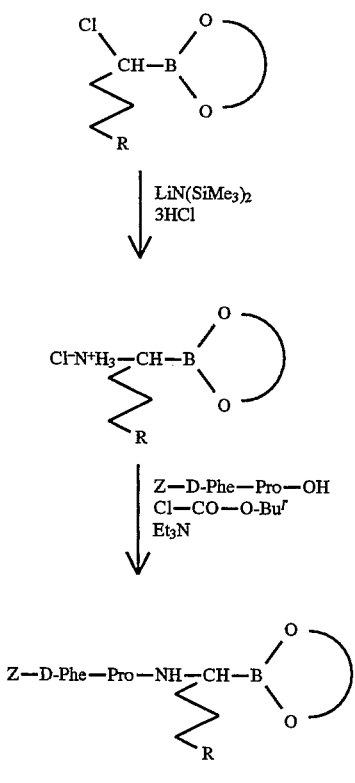
Scheme 5
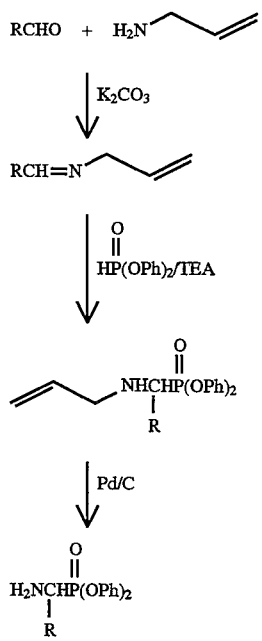
Scheme 6
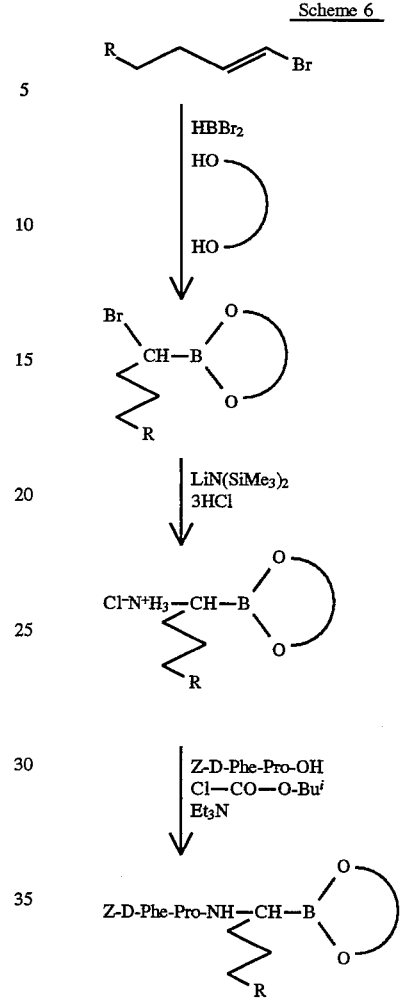
Scheme 7
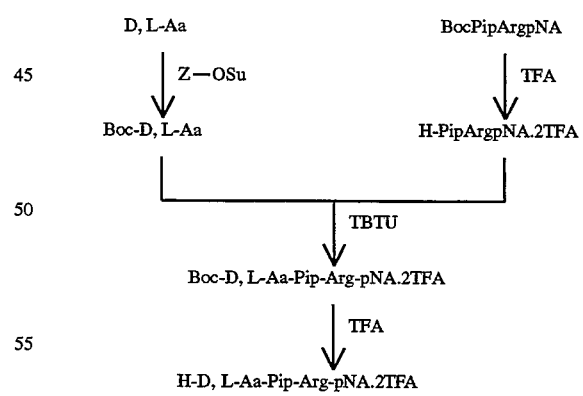
Scheme 8
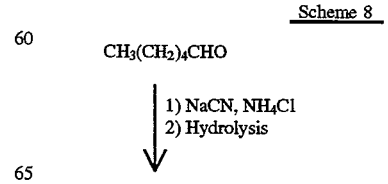

-continued
Scheme 8

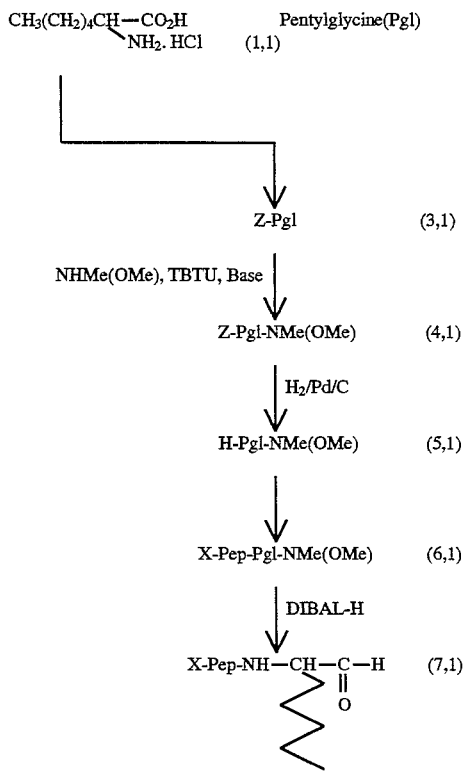

Plasma thrombin time (TT)

A volume of 150 µl of citrated normal human plasma and 20 µl of buffer or sample were warmed at 37° C. for 1 min. Coagulation was started by adding 150 ul of freshly prepared bovine thrombin (5NIHu/ml saline) and the coagulation time was recorded on a coagulometer.

A phosphate buffer, pH7.8, containing 0.1% bovine serum albumine and 0.02% sodium azide was used. The samples were dissolved in DMSO and diluted with the buffer. When no inhibitor was used DMSO was added to the buffer to the same concentration as that used in the samples. The inhibitor concentrations were plotted against the thrombin times in a semilogarithmic graph from which the inhibitor concentration that caused a doubling (40 sec) of the thrombin time was determined.

Determination of Ki

The inhibition of human α-thrombin was determined by the inhibition of the enzyme catalyzed hydrolysis of three different concentrations of the chromogenic substrate S-2238.

200 µl of sample or buffer and 50 µl of S-2238 were incubated at 37° C. for 1 min and 50 µl of human α-thrombin (0.25 NIHu/ml) was added. The initial rate of inhibited and uninhibited reactions were recorded at 405 nm. The increase in optical density was plotted according to the method of Lineweaver and Burke. The Km and apparent Km were determined and Ki was calculated using the relationship:

$$Ki = \frac{I}{\frac{Km\ app}{Km} - 1}$$

Cardiovascular effects

Cats weighing 2–3 kg were anaesthetized with Mebumal, given as an intraperitnoeal injection. The central blood pressure and heart rate were recorded on a Grass Polygraph by means of a catheter inserted in the femoral DETERMINATION OF km The km of substrates with human α-thrombin were determined by measuring the absorbance at a series of dilutions of substrate. (page 753, Longman Scientific & Technical, 5th edition, 1989.)

DETERMINATION OF ACTIVATED PARTIAL THROMBOPLASTIN TIME (APTT) FOR IN-VITRO SAMPLES

A volume of 150 µl of citrated (3.2%) normal human plasma was incubated at 37° C. with sample (20 µl) or buffer (20 µl, control) for 1 min. To the solution was added reconstituted "AUTOMATED APTT" (available from Organon Teknika, 0.1 ml). Each solution was activated at 37° C. for 5 min.

After activation, calcium chloride (0.1 ml, 0.02M, prewarmed at 37° C.) was added and clot detection was timed using a "semiautomated coagulometer" (Nach, Schnicter und Gross).

IN-VIVO TOXICITY DATA

Deposition of [111]indium-labelled platelets was monitored after 1 mg/kg intravenous doses, via a cannula in the marginal ear vein of New Zealand white rabbits, as outlined in G. R. May, C. M. Hero, K. D. BUTLER, C. P. PAGE, JOURNAL OF PHARMACOLOGICAL METHODS, 24, pp 1–35, 1990. Peripheral blood pressure was monitored by a pressure sensor in the carotid artery.

EX-VIVO APTT, TT

Data was obtained as for in-vitro tests, but using plasma samples obtained at 0,1,10,30 and 60 minutes after dosing of 1 mg/kg, i.v. bolus injection in a marginal ear vein in New Zealand white rabbits, which were anaesthetized from a canula in the carotid artery.

Mty 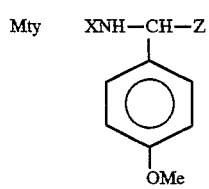

Npg 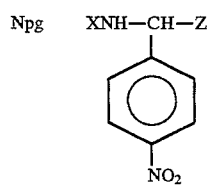

Cpg 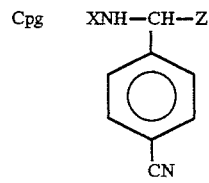

Epg 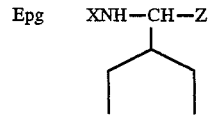

Dpg 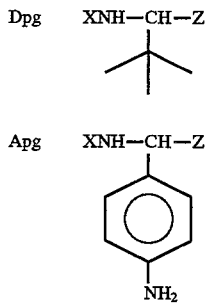

Apg

Pyg 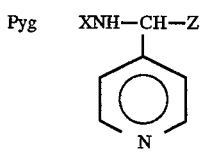

| | PLATELET ACCUMULATION | | BLOOD PRESSURE |
|---|---|---|---|
| Compound | (% OF NORMAL) LUNG | LEG | Δ% of NORMAL |
| 4 mg/kg iv. DOSE | | | |
| No. 25 ZD-PheProBoroIrgOPin | FATAL PLATELET ACCUMULATION 100% | FATAL ACCUMULATION 100% | 100% |
| No. 53 BocDPhePro His—H | NONE | NONE | 0 |
| No. 22 ZDPheProBoroMbgOPin | NONE | 11%, TRANSIENT | 0 |
| No. 41 ZDPheProBoroPheOPin | NONE | NONE | 21% |
| 1 mg/kg i.v. DOSE | | | |
| No. 59 ZDPheProBoroMbgOPin | NONE | NONE | NONE |
| No. 25 ZDPheProBoroIrgOPin | 44–40%, PROLONGED | 44–40% | SMALL |
| No. 20 H-D-PheProPgl$^F$(OPh)$_2$ | NONE | NONE | NONE |
| No. 53 BocDPheProHis—H | NONE | NONE | NONE |
| No. 6 H-D-DpaProArg-k-Gly-pip | NONE | NONE | NONE |

| EX-VIVO DATA | T.T. | | | | A.P.T.T. | | | |
|---|---|---|---|---|---|---|---|---|
| ANIMAL | 1 | | 2 | | 1 | | 2 | |
| COMPOUND NO. 6. | | | | | | | | |
| TIME (MIN) | | | | | | | | |
| 0 | 24.4 | 25.6 | 32.9 | 27.9 | 24 | | 57 | |
| 1 | 176 | 200 | 260 | >200 | 46 | | 78 | |
| 10 | 55 | 61.4 | 76 | 57.5 | 32 | | 55 | |
| 30 | 33 | 36.9 | 62 | 36 | 34 | | 57 | |
| 60 | 25 | 27.9 | 49 | 31.5 | 27 | | 42 | |
| COMPOUND NO. 11 | | | | | | | | |
| TIME (MIN) | | | | | | | | |
| 0 | 30 | 24.5 | 26 | | 46.5 | | 26.4 | |
| 1 | >300 | >200 | >300 | | UC | | UC | |
| 10 | >300 | >200 | >300 | | UC | | UC | |
| 30 | 102 | >200 | >300 | | 236.7 | | 49 | |
| 60 | 94 | >200 | >300 | | 53.0 | | 38.4 | |
| COMPOUND NO. 59 | | | | | | | | |
| TIME (MIN) | | | | | | | | |
| 0 | 28.9 | 22.5 | 22.4 | 23.5 | 42 | 59.5 | 43.9 | 58 |
| 1 | 111 | 106 | 171.5 | 168.5 | 111.4 | 111 | 102.9 | 126 |
| 10 | 35.9 | 34 | 37.9 | 38.4 | 48.9 | 53 | 60.5 | 67 |
| 30 | 29 | 30 | 32 | 31 | 34.9 | 49 | 59 | 53.9 |
| 60 | 28.4 | 28.5 | 27.9 | 28 | 40.4 | 48.4 | 65.5 | 62 |
| COMPOUND NO. 53 | | | | | | | | |
| TIME (MIN) | | | | | | | | |
| 0 | 26 | 27 | 24 | 24.9 | 32.9 | | 24.9 | |
| 1 | 86.9 | 83.5 | 80.9 | 74 | 41.5 | 41.5 | 27.9 | 30.9 |

-continued

PLATELET ACCUMULATION

| 10 | 32 | 32 | 30 | 29.9 | 39.9 | 29.9 | 26 | 25.9 |
|----|------|------|------|------|------|------|------|------|
| 30 | 24.4 | 25 | 25.9 | 25.4 | 31.4 | 30.4 | 25.4 | 26.1 |
| 60 | 24.4 | 23.9 | 22.9 | 22.9 | 28.9 |  | 27.5 | 25.9 |

|  | IC50 |  | Plasmin | Xa | Urokinase | Kallikrein | Chymotrypsin |
|---|---|---|---|---|---|---|---|
|  | No incubation | Inc. | no inc/inc | no inc/inc | no inc/inc | no inc/inc | no inc/inc |
| 15 Boc-Dpa—Pro—Pgl$^P$(OH)$_2$ | 5.28 | 0.0836 |  |  |  |  |  |
| 16 D,L-Dpa—Pro—Pgl$^P$(OH)$_2$ | 5.16 | 0.0817 |  |  |  |  |  |
| 18 D-Dpa—Pro—Pgl$^P$(OH)$_2$ | 148.0 | 0.151 |  |  |  |  |  |
| 19 Z-D-Phs—Pro—Pgl$^P$(OPh)$_2$ | 149.0 | 0.0187 |  |  |  |  |  |
| 21 D-Phe—Pro—Pgl$^P$(OH)$_2$ | non(137.0) | 4.35 |  |  |  |  |  |
| 23 D-Dpa—Pro—Pgl$^P$(OPh)$_2$ | 0.187 | 0.000938 |  |  |  |  |  |
| 32 H-D-Dpa—Pro—Mpg$^P$(OPh)$_2$ | 1.48 | 0.00235 | n(187.0)/3.32 | 39.7/n18.7 | 83.0/n18.7 | 66.7/n18.7 | n18.7/0.000149 |
| 40 H-D-Phe—Pro—Mpg$^P$(OPh)$_2$ | 16.6 | 0.0118 | n20.9/52.5 | n20.9/n20.9 | n20.9/n20.9 | n20.9/n20.9 | n20.9/0.00263 |
| 55 H-D-Phe—Pro—Apg$^P$(OPh)$_2$ |  | 3.96 |  |  |  |  |  |
| 56 H-D-Phe—Pro—Epg$^P$(OPh)$_2$ |  | 0.117 |  |  |  |  |  |
| 57 H-D-Phe—Pro—DPg$^P$(Oph)$_2$ |  | 0.0828 |  |  |  |  |  |
| 22 Z-D-Phe—Pro—BoroMbg—OPinac | 0.007 |  | 11.5 | 3.86 | 9.13 | 12.9 |  |
| 41 Z-D-Phe—Pro—BoroPbg—OPinac | 0.0128 |  | 37.3 | 7.94 | 6.67 | 16.7 |  |
| 50 Z-D-Phe—Pro—BoroMpg—OPin | 0.0007 |  | 3.23 | 1.72 | 3.63 | 7.26 |  |
| 6 D-Dpa—Pro—Arg—k—Gly—Pip | 0.2 |  | n(157.0) | 149.0 | 494.0 | 199.0 |  |
| 44 Bzl—Pro—BoroIrg—OPin | 1.3 |  | 0.153 | 0.512 | 0.121 | 1.08 |  |
| 25 Z-D-Phe—Pro—BoroIrg—OPin | 1.5 |  | 0.0084 | 0.0141 | 0.075 | 0.334 |  |
| 52 Boc-D-Phe—Pro—His—H |  |  | n(413.0) | n(413.0) | n(413.0) | non(413.0) |  |

References

1. Claeson, G. and Aurell, L. Annals of New York Academy of Sciences, 370, 79–811 (1981).
2. Bajusz, S., Barabas, E., Tolnay, P. et al. Int. J. Peptide Protein Res. 12, 217–221 (1978).
3. Kettner, C. and Shaw, E. Thrombosis Research 14, 969–973 (1979).
4. Szelke, M. and Jones, D. M. U.S. Pat. No. 4,638,047-A.
5. Kettner, C. and Shenvi, A. B. European patent appl. 293881 (1988).
6. Stüber, W., Kosina, H. and Heimburger, N. Int. J. Peptide Protein Res. 31, 63–70 (1988).
7. Kaiser, B., Hauptmann, J. and Markwardt, F. Die Pharmacie 42, 119–121 (1987).

We claim:

1. A peptide of the formula

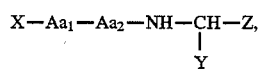

wherein

X=H, CH$_3$ or an N-protecting group;

Y=C$_3$–C$_9$ alkyl optionally substituted by C$_1$–C$_4$ alkoxy;

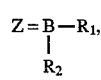

where R$_1$ and R$_2$ taken together represent the residue of a diol;

Aa$_1$=Dpa, Nal or Dba; and

Aa$_2$=proline.

2. A peptide according to claim 1 which is selected from the following:

Cbz-D-Dpa-Pro-boroPgl pinacol ester

Ac-D-βNal-Pro-boroMbg pinanediol ester and

Cbz-D-Dpa-Pro-boroMpg-pinanediol ester.

3. A peptide according to claim 1 which is a substrate of thrombin.

4. A peptide according to claim 1 which is an inhibitor of thrombin.

5. A peptide according to claim 1, wherein Aa1 is Dpa.

6. A peptide according to claim 5, wherein Y— is MeOCH$_2$CH$_2$CH$_2$—.

7. A peptide according to claim 1, wherein R$_1$ and R$_2$ taken together represent the residue of pinacol or pinanediol.

8. A peptide according to claim 6, wherein R$_1$ and R$_2$ taken together represent the residue of pinacol or pinanediol.

9. A peptide according to claim 8, wherein R$_1$ and R$_2$ taken together represent the residue of pinacol.

10. A peptide according to claim 9 wherein X is Cbz.

11. A pharmaceutical composition comprising a peptide according to claim 1 and a pharmaceutically acceptable carrier or diluent.

12. A pharmaceutical composition according to claim 11, wherein said peptide has the formula:

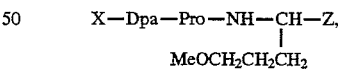

wherein

X=H, CH$_3$ or an N-protecting group;

R$_1$ and R$_2$ taken together represent the residue of pinacol or pinanediol.

13. A method of inhibiting thrombin in a mammalian host, comprising administering to the host a thrombin inhibiting effective amount of a peptide according to claim 1.

14. A method according to claim 13, wherein the peptide is administered in combination with a pharmaceutically acceptable carrier or diluent.

15. A method according to claim 14, wherein Aa1 is Dpa.

16. A method according to claim 15, wherein Y—MeOCH$_2$CH$_2$CH$_2$—.

17. A method according to claim 15, wherein R$_1$ and R$_2$ taken together represent the residue of pinacol or pinanediol.

18. A method according to claim 16, wherein R$_1$ and R$_2$ taken together represent the residue of pinacol or pinanediol.

19. A method according to claim 17, wherein R$_1$ and R$_2$ taken together represent the residue of pinacol.

20. A method according to claim 19 wherein X is Cbz.

21. A method according to claim 13 wherein the peptide is selected from the following:

Cbz-D-Dpa-Pro-boroPgl pinacol ester

Ac-D-βNal-Pro-boroMbg pinanediol ester and

Cbz-D-Dpa-Pro-boroMpg-pinanediol ester.

22. A method according to claim 13, wherein the peptide is administered at a dose of from 0.02 to 15 mg/kg of body weight.

23. A method according to claim 22, wherein the dose is from 1 to 10 mg/kg of body weight.

24. A method according to claim 13, wherein the peptide is administered as a single dose or in divided doses or as a sustained release formulation.

25. A method according to claim 13, wherein the host is a human host.

26. A method of preventing coagulation of mammalian blood, comprising adding thereto a thrombin inhibiting effective amount of a peptide according to claim 1.

27. A method according to claim 26, wherein the amount of peptide added is from 1 to 10 mg/liter.

28. A method of establishing an extracorporeal blood loop for a patient, comprising administering intravenously from 0.1 to 1 mg/kg of body weight of a peptide according to claim 1.

29. A method of inhibiting the activity of thrombin comprising contacting thrombin with a peptide according to claim 1.

* * * * *